United States Patent [19]

Abramson

[11] 4,166,467

[45] Sep. 4, 1979

[54] BITE BLOCK FOR ENDOTRACHEAL TUBE

[75] Inventor: Harvey J. Abramson, New York, N.Y.

[73] Assignee: Metatech Corporation, Northbrook, Ill.

[21] Appl. No.: 822,562

[22] Filed: Aug. 8, 1977

[51] Int. Cl.² ............................................. A61M 25/00
[52] U.S. Cl. ....................................... 128/351; 128/12; 128/145.5; 128/208
[58] Field of Search ....................... 128/12, 136, 145.5, 128/208, 348-351

[56] References Cited

U.S. PATENT DOCUMENTS

| | | | |
|---|---|---|---|
| 2,463,149 | 3/1949 | Caine | 128/351 |
| 2,693,182 | 11/1954 | Phillips | 128/208 |
| 2,981,254 | 4/1961 | Vanderbilt | 128/349 B |
| 3,090,122 | 5/1963 | Erickson | 128/12 X |
| 3,908,665 | 9/1975 | Moses | 128/351 |
| 3,946,742 | 3/1976 | Eross | 128/351 |

*Primary Examiner*—Dalton L. Truluck

*Attorney, Agent, or Firm*—Leydig, Voit, Osann, Mayer & Holt, Ltd.

[57] ABSTRACT

An endotracheal tube assembly which includes a curved section of flexible tubing suitable for insertion into the trachea and having a junction fitting at its outer end extending outside of the mouth of the patient, the junction fitting providing a male connection having an interference fit with the tubing so that the tubing is stretched and enlarged in the region of overlap. The assembly is distinguished by bite block in the form of a ferrule of relatively soft resilient plastic having an inner diameter greater than the diameter of the tubing while providing a snug frictional fit with the tubing concentrated at its outer end in the region of overlap. The bite block has substantially parallel top and bottom surfaces for safe gripping by the teeth of the patient, interconnected by side walls of sufficient thickness as to prevent collapse of the tube upon clenching of the teeth. The bite block is sufficiently long so as to permit adjustment of the degree of insertion of the tube in accordance with radiological observation while keeping the bite block within biting range.

4 Claims, 4 Drawing Figures

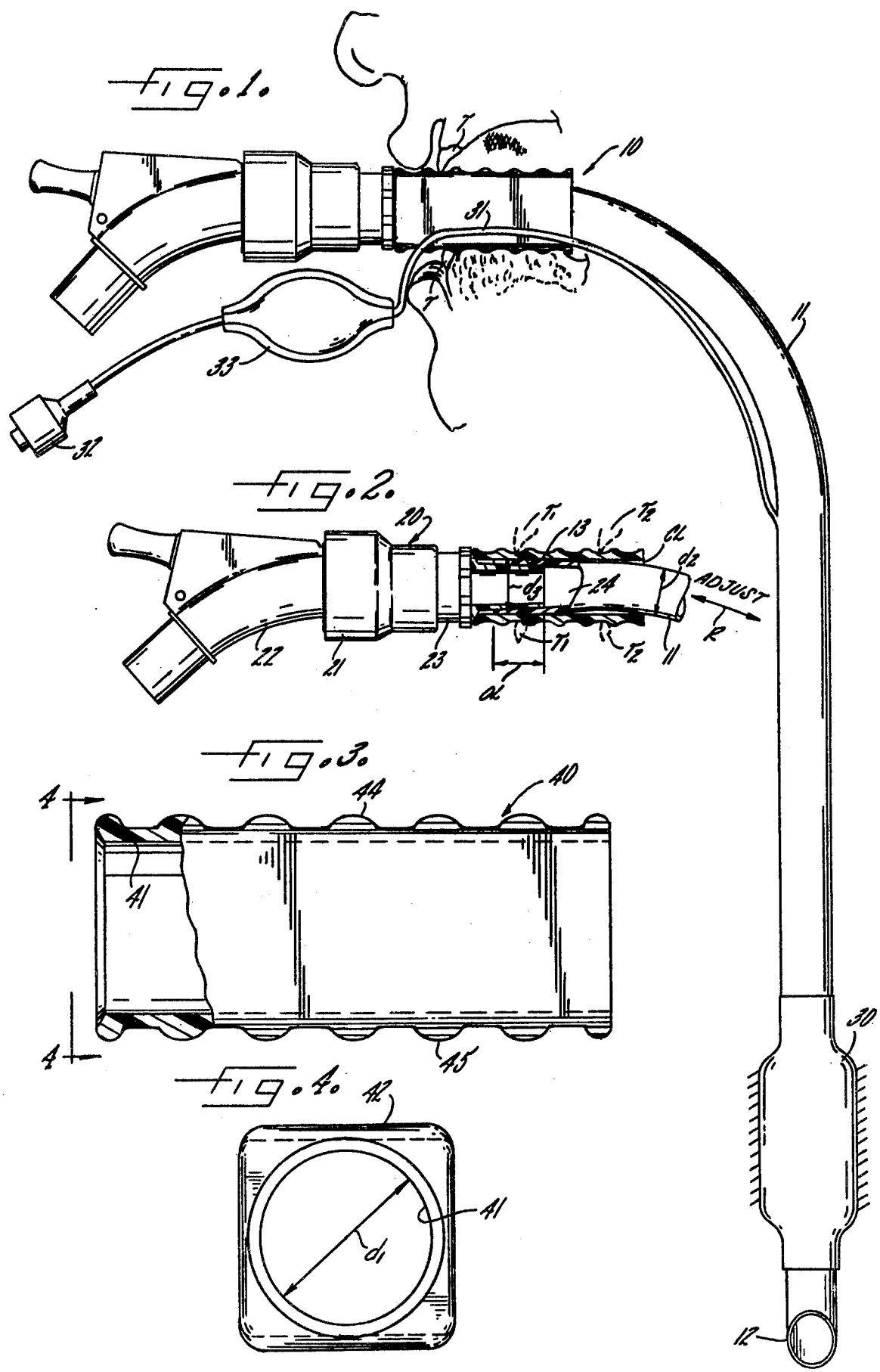

BITE BLOCK FOR ENDOTRACHEAL TUBE

Insertion, adjustment and retention of an endotracheal tube is often a difficult ordeal both for the medical staff and for the patient. The tubing, which comes in standard lengths, is tailored approximately to the patient, and a junction fitting providing a male connection, and usually made of hard plastic or metal, is attached to the outer end. After insertion the assembly is adjusted either upwardly or downwardly within the trachea, with the medical technician being guided by the relative position of a radiologically opaque spot normally placed at the lower end of the tube. There is very little leeway for this adjustment; if the tubing is found to be short it is more deeply inserted, bringing the fitting at least partially into the mouth of the patient to cause discomfort. Thus when the patient either voluntarily or involuntarily clenches his teeth, he risks breakage of a front tooth on the hard fitting. Conversely, if the tubing is slightly retracted, voluntary or involuntary clenching can cause the teeth to collapse the flexible tubing to cut off the flow which, in the case of supplying of oxygen or the like, may have disastrous effects.

It is, accordingly, an object of the present invention to provide an endotracheal tube assembly which insures against cutting off of the endotracheal flow as a result of biting or clenching of the teeth. It is another object of the present invention to provide an endotracheal tube assembly which is safe and comfortable for the patient, which prevents damage to the teeth, and which provides a soft and relaxing "bite", giving the patient a feeling of security that the tube will not move in or out as a result of swallowing motions or as a result of bodily movement. Thus it is an object to provide an endotracheal tube assembly which may be kept in place, without discomfort, for longer periods of time than is normally the case.

It is another object of the invention to provide, in an endotracheal tube assembly, a bite block which is reliably retained by friction localized at the upper end of the tube and which may, nevertheless, be quickly and easily assembled and disassembled by a combination of rocking and twisting movement. Not only is the bite block reliably held in position on the tube, but the tube, by reason of the bite block, becomes more positively and reliably clamped to the junction fitting.

It is a related object to provide, as an element of an improved endotracheal assembly, a bite block which is simple and inexpensive to manufacture, which is highly reliable over a wide range of dimensional tolerance, and which may be indefinitely re-used or treated as disposable depending upon the surgical control procedures which are in effect.

It is yet another object of the present invention to provide an endotracheal tube assembly employing a bite block which is not only comfortable to the patient but which accommodates a wide range of adjustment in the length, or degree of insertion, of the tubing so that the lower tip of the tubing can, with radiological guidance, be located in an optimum position. Thus it is an object to provide a bite block having a plurality of ribs or corrugations which may be selectively engaged by the teeth of the patient and which serve to hold the tube indefinitely in a precisely adjusted position.

Other objects and advantages of the invention will become apparent upon reading the attached detailed description and upon reference to the drawings in which:

FIG. 1 shows an endotracheal tube assembly constructed in accordance with the present invention;

FIG. 2 shows a portion of the assembly in cross section to reveal internal detail and to show range of adjustment;

FIG. 3 is an elevational view, in partial section, and on an enlarged scale, of the bite block employed in the assembly of FIGS. 1 and 2;

FIG. 4 is an end view looking along line 4—4 in FIG. 3.

While the invention has been described in connection with a preferred embodiment, it will be understood that I do not intend to be limited to the particular embodiment shown, but intend, on the contrary, to cover the various alternative and equivalent constructions covered within the spirit and scope of the appended claims.

Turning now to the drawing, there is shown an endotracheal tube assembly 10 which includes a length of tubing 11, preferably of soft, flexible plastic such as vinyl, having a lower end 12 and an upper end 13. At its upper end the tubing is connected to a junction fitting 20 having relatively swivelling parts 21, 22. The fitting includes a nipple 23 having a standard tapered joint with the part 21 and having a male connection 24, the latter being fitted into the upper end of the tubing. The male connection 24 has a slight interference fit with respect to the inner wall of the tubing; that is to say, the maximum outer diameter of the connection exceeding the diameter of the tubing, preferably by having a taper on the outer surface of the male connection, so that the tubing, upon being installed, is stretched and enlarged in the region of overlap, OL.

For sealing the tube with respect to the wall of the trachea, and for assisting and holding it in adjusted position, the tubing is provided with an inflatable annulus or "cuff" 30 formed of thin latex and having a light gauge pressure conduit 31. The latter is, over a portion of its length, integrated with the wall of the tubing and has, at its inlet end, a combined check valve and coupling 32. The latter may be constructed as set forth in my copending application Ser. No. 815,598, filed July 14, 1977, now U.S. Pat. No. 4,143,853, issued Mar. 3, 1979. It will suffice to say that the coupling 32 accepts a rudimentary form of piston pump for inflating the cuff and for thereafter holding the pressure until intentional release. Included in series with the conduit 31 is a small bladder 33 which acts as a tell-tale, with its inflated condition constantly indicating that pressure is being held at the desired level.

In carrying out the present invention a bite block is provided as part of the assembly in the form of a ferrule of relatively soft resilient plastic which is telescoped over the tubing from the region of overlap, OL, inwardly into the mouth of the patient, the bite block having an inner diameter greater than the outer diameter of the tubing for free sliding movement thereof while providing a snug frictional fit with the tubing at the enlargement of the region of the overlap, the bite block being sufficiently long so as to permit adjustment of the degree of insertion of the tubing while keeping the bite block within biting range. Thus, referring to the drawing, the bite block, indicated at 40, has a cylindrical internal wall 41 and an outer surface of "square" configuration providing parallel top and bottom surfaces 42, 43, respectively, provided with laterally extending ribs or corrugations 44, 45. The bite block has a constant internal diameter $d_1$ which exceeds the nominal diameter $d_2$ of the tubing, thereby making the bite block freely slidable on the tubing and providing a normal clearance CL therebetween. However, in the region of the overlap, OL, the tubing is stretched and enlarged to a maximum outer diameter $d_3$ which slightly exceeds the diameter $d_1$. Consequently the bite block, notwithstanding its free slidability on the tubing, it is snugly and frictionally engaged at its outer end, engaged with sufficient force as to prevent axial dislodgement from its working position. Because of the fact that the bite block is frictionally gripped only at its end, and because of the fact that the region of overlap is limited, only a small amount of intentional movement, accompanied by a combined rocking and twisting action, suffices to move the bite block between its free and working positions, thereby greatly simplifying both assembly and disassembly. Because the engagement between the bite block and the tubing is concentrated or localized at the expanded end of the tubing, the internal diameter dimension $d_1$ of the bite block need not be precise and may vary over a rather wide tolerance range without affecting the operation or security of the device.

It is one of the features of the construction that the bite block is sufficiently long, with lateral corrugations 44, 45 distributed over a sufficient distance, as to permit a substantial variation in the degree of insertion of the tubing, while keeping the bite block within the range of bite.

In use, the tubing 11 and the junction fitting 20, with its nipple 23 are separately supplied and the tubing is trimmed, as its end 13, to an estimated insertion length. The bite block 40 is telescoped over the tubing and the male connection 24 is inserted into the presented end of the tubing. Because of the interfering fit, in other words, because of the taper of the member 24, the tubing in the region of overlap is stretched and enlarged, expanding to a diameter $d_3$ which is sufficiently great so that when the bite block is pressed into position over the overlap, it is not only securely retained but serves also, by pressing inwardly upon the tubing, to seat the tubing more firmly against the male connection, thereby improving the integrity of the entire assembly.

The assembly is next inserted into the mouth of the patient between the opposed teeth and down into the trachea, with the tube being adjusted to a precise position by radiological observation of an opaque spot (not shown) at the end of the tube. At this time the patient is informed that he may bite down upon the bite block in order to hold it in place, and the inflatable cuff 30 is pumped up through the valve 32, the cuff forming a seal between the tubing and the wall of the trachea. It is to be noted that the corrugations 44, 45 are distributed over such a length as to provide a range of alternative biting positions T1, T2 resulting in a range of adjustment in excess of that indicated at R, for movement of the tubing upwardly and downwardly, either as a matter of initial adjustment or when it is desired to readjust the depth of insertion.

Having something soft and resilient to bite down upon not only gives the patient satisfaction but it provides him with a feeling of security that the tube will not shift in position.

It will be apparent to one skilled in the art that the features and advantages of the invention are not limited to any particular bite block material. A soft rubber-like material having durometer rating between 50 and 70 may be used, with polyethylene, because of its durability, economy, and good molding qualities, being preferred. The term "plastic" as used herein should be considered broad enough to include natural or artificial rubber.

It is apparent that the objects of the invention, stated above, have been adequately carried out. Both safety and comfort are enhanced. Not only are the patient's teeth protected against breakage, but biting down on the tube itself is precluded so that continuous flow is assured. The tubing need be cut only to approximate length and may be thereafter adjusted over a wide range for optimum positioning, with the precise position being reliably maintained. Using the present invention, the junction fitting may be caused to project sufficiently from the mouth of the patient to facilitate the making of connections with associated apparatus, particularly where the fitting has swivelling capability.

It is one of the features of the present invention that the bite block is of a particular size, being approximately ⅝ inch square in cross section and having a length which is preferably 1¼ inches but with which should not, in any event, be less than an inch or greater than two inches. And while the use of ribs is preferred on the top and bottom surfaces, it will be understood that the term "corrugation" is not necessarily limited to continuous ribs and that any pattern of surface irregularity may be used which promotes a registered condition between the teeth and the block.

I claim:

1. An endotracheal tube assembly comprising, in combination, a curved section of flexible tubing suitable for insertion into the trachea and having a junction fitting at its outer end, the junction fitting being made of hard plastic and substantially larger in diameter than the tubing and extending outside of the mouth of the patient, the junction fitting providing a male connection for the tubing adjacent the lips of the patient, the tubing having an interference fit in the region of overlap with the male connection so that the tubing is stretched and enlarged in the region of overlap, a bite block in the form of a ferrule of relatively soft resilient plastic telescoped over the tubing and extending from the region of overlap inwardly into the mouth of the patient, the bite block having an inner diameter greater than the diameter of the tubing for free sliding movement thereon while providing a snug frictional fit with the tubing at the enlargement in the region of overlap, the bite block having substantially parallel top and bottom surfaces for gripping by the teeth of the patient, the walls of the bite block being sufficiently thick so as to preclude collapsing of the tube upon clenching of the teeth.

2. An endotracheal tube assembly comprising, in combination, a curved section of flexible tubing suitable for insertion into the trachea and having a junction fitting at its outer end, the junction fitting being made of hard plastic and substantially larger in diameter than the tubing and extending outside of the mouth of the patient, the junction fitting providing a male connection for the tubing adjacent the lips of the patient, the tubing having an interference fit in the region of overlap with the male connection so that the tubing is stretched and enlarged in the region of overlap, a bite block the form of a ferrule of relatively soft resilient plastic telescoped over the tubing and extending from the region of overlap and inwardly into the mouth of the patient, the bite block having (a) a cylindrical inner wall having clearance with respect to the tubing while providing a snug frictional fit with the tubing at the enlargement thereof in the region of overlap and (b) a square outer cross section defining substantially parallel top and bottom surfaces formed with transversely extending corrugations for gripping by the teeth of the patient, the lateral walls of the bite block being sufficiently thick so as to preclude collapsing of the tube upon clenching of the teeth, the bite block being sufficiently long as to permit adjustment of the degree of insertion of the tubing by radiological observation while keeping the bite block within the range of biting position.

3. An endotracheal tube assembly comprising, in combination, a curved section of flexible tubing suitable for insertion into the trachea and having a junction fitting at its outer end, the junction fitting being made of hard plastic and substantially larger in diameter than the tubing and extending outside of the mouth of the patient, the junction providing a tapered male connection for the tubing adjacent the lips of the patient, the tubing having an interference fit in the region of overlap with the male connection so that the tubing is stretched and enlarged in the region of overlap, a bite block in the form of a ferrule of relatively soft resilient plastic telescoped over the tubing and extending over the region of overlap and inwardly into the mouth of the patient, the bite block having (a) a cylindrical inner wall having clearance with respect to the tubing while providing a snug frictional fit with the tubing at the enlargement thereof in the region of overlap and (b) an outer cross section defining substantially flat and parallel top and bottom surfaces formed with shallow transversely extending corrugations for gripping by the teeth of the patient, the lateral walls of the bite block being sufficiently thick so as to preclude collapsing of the tube upon clenching of the teeth, the bite block being more than one inch but less than two inches in length so as to permit adjustment of the degree of insertion of the tubing by radiological observation while keeping the bite block within the range of biting position.

4. In an endotracheal tubing suitable for insertion into the trachea and having a junction fitting at its outer end providing a male connection for the tubing adjacent the lips of the patient and with the tubing having an interference fit so that the tubing is enlarged in the region of overlap with the male connection, the improvement comprising a bite block in the form of a ferrule of relatively soft resilient plastic having a cylindrical inner wall providing a snug frictional fit with the tubing at the enlargement in the region of overlap and having a square outer cross section defining substantially top and bottom surfaces formed with transversely extending corrugations for gripping by the teeth of the patient, the bite block having a cross sectional outer dimension on the order of ⅝ inch and having a length on the order of 1½ inches, the bite block being formed of resilient material having a durometer rating between 50 and 70 and having sufficient lateral wall thickness so as to prevent collapse of the tubing upon clenching of the teeth at any point along the length of the bite block.

* * * * *